(12) United States Patent
Lei (10) Patent No.: US 11,311,653 B2
(45) Date of Patent: Apr. 26, 2022

(54) CENTRAL VENOUS CATHETER, PREPARATION METHOD THEREFOR AND MEDICAL DEVICE COMPRISING SAME

(71) Applicant: Jiangsu Biosurf Biotech co., Ltd., Jiangsu (CN)

(72) Inventor: Jiehua Lei, Jiangsu (CN)

(73) Assignee: JIANGSU BIOSURF BIOTECH CO., LTD., Jiangsu (CN)

( * ) Notice: Subject to any disclaimer, the term of this patent is extended or adjusted under 35 U.S.C. 154(b) by 0 days.

(21) Appl. No.: 17/427,716

(22) PCT Filed: Nov. 7, 2019

(86) PCT No.: PCT/CN2019/116232
§ 371 (c)(1),
(2) Date: Aug. 2, 2021

(87) PCT Pub. No.: WO2020/155733
PCT Pub. Date: Aug. 6, 2020

(65) Prior Publication Data
US 2022/0040384 A1 Feb. 10, 2022

(30) Foreign Application Priority Data
Feb. 2, 2019 (CN) .......................... 201910107797.8

(51) Int. Cl.
*A61L 29/14* (2006.01)
*C08K 5/14* (2006.01)
(Continued)

(52) U.S. Cl.
CPC .............. *A61L 29/085* (2013.01); *A61L 29/14* (2013.01); *C08K 5/07* (2013.01); *C08L 39/06* (2013.01); *A61L 2420/06* (2013.01)

(58) Field of Classification Search
None
See application file for complete search history.

(56) References Cited

U.S. PATENT DOCUMENTS

| 9,447,304 | B2* | 9/2016 | Drumheller | A61L 29/085 |
| 2005/0059086 | A1* | 3/2005 | Huang | B01J 20/286 |
| | | | | 506/9 |

(Continued)

FOREIGN PATENT DOCUMENTS

| CN | 102947376 A | 2/2013 |
| CN | 105263535 A | 1/2016 |

(Continued)

OTHER PUBLICATIONS

Google scholar search, catheter and lysine and benzophenone (Year: 2021).*

(Continued)

*Primary Examiner* — Peter A Salamon
(74) *Attorney, Agent, or Firm* — Fox Rothschild LLP (57) ABSTRACT

The disclosure relates to a central venous catheter, preparation method thereof and a medical device having the same. The central venous catheter comprises a tube body and a coating formed on the surface of tube body, coating being formed of a coating composition comprising at least one photosensitive functional compound and at least one photocurable polymer. The central venous catheter of the disclosure can prevent thrombosis, dissolve primary thrombus, and possess super-lubricated surface and firm coating bonding.

17 Claims, 2 Drawing Sheets

(51) Int. Cl.
    *A61L 29/08*    (2006.01)
    *C08K 5/07*     (2006.01)
    *C08L 39/06*    (2006.01)

(56) References Cited

U.S. PATENT DOCUMENTS

| | | | | |
|---|---|---|---|---|
| 2006/0183863 A1* | 8/2006 | Huang | ................ | C08F 220/387 |
| | | | | 525/234 |
| 2006/0292701 A1* | 12/2006 | Huang | ................ | C08B 37/0021 |
| | | | | 436/514 |
| 2007/0003588 A1* | 1/2007 | Chinn | .................... | A61L 27/34 |
| | | | | 424/423 |
| 2007/0043160 A1* | 2/2007 | Hanley | .................. | A61L 31/10 |
| | | | | 524/502 |
| 2007/0082019 A1* | 4/2007 | Huang | ................ | H01J 49/0418 |
| | | | | 424/423 |
| 2013/0202833 A1* | 8/2013 | Belt | .................... | C10M 135/34 |
| | | | | 428/36.91 |

FOREIGN PATENT DOCUMENTS

| | | | |
|---|---|---|---|
| CN | 105963796 | A | 9/2016 |
| CN | 107405424 | A | 11/2017 |
| WO | 2001021326 | A1 | 3/2001 |
| WO | 2004076511 | A2 | 9/2004 |

OTHER PUBLICATIONS

International Search Report dated Aug. 6, 2020 in related PCT Application No. PCT/CN2019/116232, 10 pages.

* cited by examiner

CENTRAL VENOUS CATHETER, PREPARATION METHOD THEREFOR AND MEDICAL DEVICE COMPRISING SAME

CROSS-REFERENCE TO RELATED APPLICATIONS

The present application is a U.S. National Phase of International Patent Application No. PCT/CN2019/116232, filed on Nov. 7, 2019, which claims priority to Chinese Patent Application No. 201910107797.8, filed on Feb. 2, 2019. The contents of the listed patent documents are incorporated herein by reference in their entireties.

TECHNICAL FIELD

The disclosure belongs to the field of medical devices, in particular to the field of central venous catheters with hydrophilic lubricious coatings.

BACKGROUND

Central venous catheter (CVC) is a very common medical device, which is inserted into the patient's vein by puncture for diagnosis and treatment such as central venous pressure measurement, intravenous is infusion, long-term drug injection, hemodialysis and tumor chemotherapy. Central venous catheter can be placed in the blood vessels of patients with poor peripheral vascular conditions or requiring long-term infusion for a long time. However, complications caused by long-term indwelling, especially the formation of catheter-related thrombus, limit the further application of catheter. According to investigation, the incidence of thrombosis by central venous catheter is as high as 28.3%, which is the main reason for its application failure.

At present, the main method to prevent thromboembolism clinically is to seal the catheter with heparin. However, repeated sealing of catheter with heparin not only increases the medical expenses of patients, but also raises the risk of massive hemorrhage when a large amount of heparin is continuously released into the blood. Clinically, in order to treat catheter blockage caused by thromboembolism and fibrin encapsulation, urokinase is usually repeatedly used for thrombolysis after thrombosis, nevertheless, this method of treatment is less effective and expensive. In addition, the use of urokinase easily brings complications such as systemic hemorrhage and endangers the life of patients. Therefore, there is an urgent need in clinic for a central venous catheter which can both prevent thrombosis and dissolve primary thrombus, so as to prolong the indwelling time of central venous catheter and improve the working efficiency of medical staff.

On the other hand, the hardness and surface lubricity of catheters are important factors which have influences on vascular injury. The materials of medical central venous catheter are mainly polyurethane and medical silica gel. The surface lubricity of unmodified polyurethane or medical silica gel is generally poor, which easily causes damage to the inner wall of blood vessels during catheter insertion and removal. At present, hydrophilic polymer coating is generally used to lubricate the surface of central venous catheter, but the firmness and lubrication effect of hydrophilic lubricious coating remains to be improved.

Document 1 discloses a central venous catheter coated with is anti-infective anticoagulant coating. In addition to anti-infective drugs, the coating liquids used in the preparation process also include hydrophilic polyvinylpyrrolidone and polyoxyethylene, which are used to improve the lubricity and the ability to resist non-specific protein adsorption of catheter surface. However, in this patent, the anti-adsorption performance of hydrophilic polymer against nonspecific protein can only tentatively prevent thrombus formation, but cannot dissolve the primary thrombus. In addition, in this patent, a functional coating is coated on the surface of the catheter by high temperature curing after dip-coating, and the firmness of the coating remains to be improved.

Therefore, there is still space for improvement in the process of surface treatment of central venous catheter.

Literature Cited

Document 1: CN105963796A

SUMMARY

Problems to be Solved by the Disclosure

In view of the above-mentioned problems in the preparation and use of central venous catheters in the art, it is an objective of the present disclosure to provide a central venous catheter capable of preventing thrombosis, dissolving primary thrombus, with super-lubricious surface and firm coating bonding; and a method for preparing the same.

It is also objective of the present disclosure to provide a medical device comprising the above-mentioned central venous catheter.

Solutions to the Problems

The above-mentioned technical problems are resolved by providing a central venous catheter characterized in that:

[1]. The central venous catheter comprises a tube body and a coating formed on the surface of the tube body, the coating being formed of a coating composition comprising at least one photosensitive functional compound and at least one photocurable polymer, wherein the is photosensitive functional compound has a structure of formula (I):

$$P\text{-}L\text{-}I \quad (I)$$

wherein
P represents a photosensitive structural part, L represents a divalent linking group, and I represents a lysine residue,
the photocurable polymer is copolymerized by ingredients including a water-soluble polymerizable photosensitive monomer and a hydrophilic monomer,
the water-soluble polymerizable photosensitive monomer comprises: 1) a unit containing a photosensitive structure; 2) a unit containing a quaternary ammonium salt structure; and 3) a unit containing an unsaturated bond structure;
the unit containing a photosensitive structure is connected to the unit containing a quaternary ammonium salt structure at least via —C(=O)—, and the unit containing an unsaturated bond structure is connected to the unit containing a photosensitive structure via the unit containing a quaternary ammonium salt structure.

[2]. The central venous catheter according to item [1], in said photosensitive functional compound:
P is derived from an aromatic ketone photosensitive structure, preferably from one of the following compounds: substituted or unsubstituted, benzophenone, acetophenone, thioxanthone, xanthone, fluorenone and derivatives thereof;

the divalent linking group L is selected from groups consisting of —CO— and —O—;

I is connected to L by a nitrogen atom in lysine.

[3]. The central venous catheter according to item [1] or [2], the photosensitive functional compound has a structure represented by the formula (II):

[4]. The central venous catheter according to any one of items [1] to is [3], wherein 1) unit containing a photosensitive structure in the water-soluble polymerizable photosensitive monomer is derived from substituted or unsubstituted α-hydroxyalkylbenzophenone photoinitiators, preferably from any one of 2-hydroxyl-2-methyl-1-phenyl-1-propanone, 1-hydroxyl-cyclohexyl-phenyl-ketone, 2-hydroxyl-4'-(2-hydroxyethoxy)-2-methylpropiophenone, 2-hydroxyl-2-methyl-1-(4-isopropylphenyl)-1-propanone, 2-hydroxyl-2-methyl-1-(4-tert-butylphenyl)-1-propanone, more preferably from 2-hydroxyl-4'-(2-hydroxyethoxy)-2-methylpropiophenone; 3) unit containing an unsaturated bond structure is selected from units containing (meth) acrylate groups.

[5]. The central venous catheter according to any one of items [1] to [4], the water-soluble photosensitive monomer has a structure of formula (III):

wherein: $R_1$=$CH_3$ or H; $R_2$ and $R_3$ are each independently selected from a linear alkyl group having 1 to 20 C atoms or a branched alkyl group having 3 to 20 C atoms; X is halogen; n=1-10; m=1-4; f=1-3; preferably, $R_2$ and $R_3$ are identical, X is bromine, n=1, m=1, f=1; more preferably, $R_2$ and $R_3$ are both methyl or ethyl, X is bromine, n=1, m=1, f=1.

[6]. The central venous catheter according to any one of items [1] to [5], wherein the hydrophilic monomer comprises one or more of the following compounds: unsaturated carboxylic acid or carboxylate, unsaturated carboxylic acid ester, unsaturated acid hydroxyalkyl ester, unsaturated anhydrides, unsaturated amide, unsaturated lactam and epoxyalkane; preferably, the hydrophilic monomer includes one or more of the following compounds: (meth) acrylic acid, (meth) acrylamide, vinylpyrrolidone, (meth) acrylate hydroxyethyl (propyl) eater, dimethacrylamide; more preferably, the hydrophilic monomer is selected from vinylpyrrolidone.

[7]. The central venous catheter according to any one of items [1] to [6], wherein the molar fraction of the water-soluble polymerizable photosensitive monomer in the photocurable polymer is 0.08-12%, preferably 0.5-8%, further preferably 3-7.5%, and more preferably from 3-5%, and most preferably 4%; the number-average molecular weight of the photocurable polymer ranges from 0.002 to 1.5 million, preferably from 0.005 to 1 million, further preferably from 0.02 to 0.8 million, more preferably from 0.05 to 0.6 million, and most preferably from 0.1 to 0.5 million.

[8]. The central venous catheter according to any one of items [1] to [7], the content of the photosensitive functional compound in the coating composition is from 10 to 50%, relative to the total dry weight.

[9]. The method for producing a central venous catheter according to any one of items [1] to [8], comprising forming the coating composition on the surface of the central venous catheter body and performing curing under light condition.

[10]. The present disclosure also provides a medical device is comprising the central venous catheter according to any one of items [1] to [8]

Technical Effects of the Disclosure

Following technical effects are achievable with the implementation of the technical solution above-mentioned:

(1) By means of the hydrophilic lubricious coating coated on the surface of central venous catheter, a catheter with super-lubricity can be obtained, which reduces the friction force on the catheter surface and avoids the damage of the inner surface of the blood vessel caused by the friction between the catheter and the inner surface of the blood vessel.

(2) By means of the hydrophilic lubricious coating coated on the surface of the central venous catheter, the anti-adsorption performance of hydrophilic polymer against non-specific protein can tentatively prevent thrombusis.

(3) The anti-adsorption performance of hydrophilic polymer against nonspecific protein alone cannot completely prevent thrombusis. In this case, lysine residue in the photosensitive functional compound can functions in dissolving primary thrombus, because lysine adsorbs plasminogen and t-PA in blood, and the latter stimulates the former to produce plasminolytic enzyme to dissolve primary thrombus generated on the surface of the catheter.

DETAILED DESCRIPTION

The technical solution of the present disclosure will be described in detail below with reference to examples.

As used herein, that term "monomer" means any chemical substance, which can be characterized by a chemical formula and has polymerizable groups (including (meth)acrylate groups) that can be polymerized into an oligomer or a polymer to increase the molecular weight. The molecular weight of the monomer can usually be calculated simply according to a given chemical formula.

Hereinafter, when a part of a molecule is described as "optionally substituted" or "substituted", this means that the part may be substituted with one or more substituents selected from C1-C6 linear chains, branched or cyclic alkyl, aryl, —OH, —CN, halogen, amine, amide, alcohol, ether, thioether, sulfone and derivatives thereof, sulfoxide and derivatives thereof, carbonic ester, isocyanate, nitrate and acrylate.

In the present disclosure, the meaning of the term "unit" not only includes functional groups (such as photosensitive groups, quaternary ammonium salt groups and unsaturated groups), but can also include additional chemical groups that have less influence on the functional groups, such as alkyl and alkylene, etc.

In the present disclosure, the term "polymer" refers to a molecule containing two or more repetitive units. Specifically, the polymer can be formed by two or more identical or different monomers, and when used in the present disclosure, the term further includes oligomers or prepolymers. In the present disclosure, the term "molecular weight" refers to number-average molecular weight (Mn), and Mn is defined as Mn measured by light scattering (optionally in combination with size exclusion chromatography SEC).

In the present disclosure, the term "photocuring" may be realized in an exemplary manner via a photoinitiation process initiated by irradiation with is light in the wavelength ranging from 100 nm to 600 nm or UV irradiation. The irradiation sources that can be used are sunlight or artificial lamps or lasers. For example, high-voltage, medium-voltage or low-voltage mercury lamps and xenon and tungsten lamps are advantageous. Likewise, excimer-based, solid-state and diode-based lasers are advantageous. A diode-based light source is generally beneficial to initiating chemical reactions.

1) The First Embodiment

In the first embodiment of the present disclosure, there provided a central venous catheter comprising a tube body and a coating formed on the surface of the tube body, the coating being formed of a coating composition comprising at least one photosensitive functional compound and at least one photocurable polymer, The photosensitive functional compound has a structure of formula (I):

P-L-I    (I)

wherein:
P represents a photosensitive structural part, L represents a divalent linking group, and I represents a lysine residue;
the photocurable polymer is copolymerized by ingredients including a water-soluble polymerizable photosensitive monomer and a hydrophilic monomer,
the water-soluble polymerizable photosensitive monomer comprises: 1) a unit containing a photosensitive structure; 2) a unit containing a quaternary ammonium salt structure; and 3) a unit containing an unsaturated bond structure;

The unit containing a photosensitive structure is connected to the unit containing a quaternary ammonium salt structure at least via —C(=O)—, and the unit containing an unsaturated bond structure is connected to the unit containing a photosensitive structure via the unit containing a quaternary ammonium salt structure.

Tube Body

In the present disclosure, the shape and material of the tube body of the central venous catheter are not particularly limited, and can be any tube body used in the art. The material suitable for preparing the tube body according to the present disclosure is selected from natural or artificial polymers, metals, and the like. It can typically be any one of the following materials: latex, polyvinyl chloride (PVC), silicone rubber, polyurethane, nylon, polyvinyl chloride, Pebax, nickel-titanium alloy, etc. Preferably, the material is selected from the group consisting of latex, polyurethane; from the point of view of lubrication effect, polyurethane is most preferred. The central venous catheter with the hydrophilic coating of the disclosure can significantly reduce the friction after 30 cycles, the lubricating performance is more stable and durable.

Photosensitive Functional Compound

The photosensitive functional compound suitable for the present disclosure has a structure of formula (I):

P-L-I    (I)

wherein P represents a photosensitive structural part, L represents a divalent linking group, and I represents a lysine residue;

Photosensitive functional compounds can generate living radicals under the irradiation of UV or visible light source, and living radicals can seize hydrogen atoms or other unstable atoms from polymers to realize polymerization and curing cross-linking. The photosensitive structure-containing part does not contain functional groups that significantly interfere with the cationic polymerization process, and can absorb light in the wavelength ranging from about 100 to about 600 nanometers (nm).

The photosensitive structural part P in the photosensitive functional compound structure of the present disclosure is derived from an aryl ketone photoinitiator structure comprising a carbonyl functional group and one or more aromatic rings, and the aryl ketone structure may further comprise a sulfur atom. More specifically, the units of the photosensitive structure is may be derived from, but not limited to the group consisting of the following compounds: substituted or unsubstituted benzophenone, acetophenone, thioxanthone, xanthone, fluorenone, anthraquinone acridone, dibenzocycloheptanone, benzil, phenylcoumarinone and derivatives thereof, etc. Preferably, they are derived from substituted or substituted benzophenone, acetophenone, thioxanthone, xanthone, fluorenone and derivatives thereof.

Typically, the part containing the photosensitive structure in the photosensitive functional compound may be benzophenone having the following general formula:

wherein $Ar_1$ and $Ar_2$ are independently selected from the group consisting of the same or different optionally substituted aryl groups, wherein the wavy lines indicate that that $Ar_2$ are connected to the lysine part by a linking group. Preferably, both $Ar_1$ and $Ar_2$ may be optionally substituted phenyl, and more preferably, both are phenyl. Benzophenone is a well-studied commercially available photoinitiator part, and the UV absorption thereof can be adjusted according to the substitution mode of aryl groups. Preferred substituents on $Ar_1$ and $Ar_2$ are electron-donating groups or atoms, such as N, O, S, amine, ester or sulfhydryl groups, which provide UV absorption at longer wavelengths, meaning that an LED lamp can be used as the UV source. In addition, $Ar_1$ and $Ar_2$ may be further connected by an S atom or others.

Preferably, the photosensitive structural part of the photosensitive functional compound of the present disclosure is benzophenone unit as described above. Inventors of the present disclosure have found that when benzophenone is used as the photosensitive structural part of the photosensitive functional compound of the present disclosure, better is photoinitiation efficiency can be achieved.

The divalent linking group L of formula (I) is used to link photosensitive structural part and lysine structural part. In some preferred embodiments, such linking groups may include —C(=O)— or —O— groups. In a further preferred embodiment of the present disclosure, the divalent linking group is linked to the nitrogen atom of lysine.

In some preferred embodiments of the present disclosure, the photosensitive functional compound has a structure represented by formula (II):

Formula (II)

For the typical synthesis method of the above formula (II), see the following steps a~c:

(a)

The above-mentioned small molecule antithrombotic component with photoinitiator is used in the coating of the present disclosure. It can dissolve primary thrombus, and at the same time can be fixed in a reactive polymer structure thanks to its reactive end. Surprisingly, it is found that the polymer coating obtained in this way does not lead to a reduction of the associativity between the coating and the substrate due to the addition of small molecule functional additive.

Photocurable Polymer

Provided in the present disclosure is also a photocurable polymer. It is is formed by copolymerizing a water-soluble polymerizable photosensitive monomer and a hydrophilic monomer, its photosensitive structural unit can serve as a macromolecular photoinitiator, thus the use of the small molecular photoinitiator can be reduced when preparing the coating composition, and the problems of residence and migration of the small molecular photoinitiator in the coating can be overcome. The biosafety and compatibility of the small molecular photoinitiator are excellent, so the coating composition is applicable in the medical field.

Water-Soluble Polymerizable Photosensitive Monomer

The water-soluble polymerizable photosensitive monomer comprises: 1) a unit containing a photosensitive structure; 2) a unit containing a quaternary ammonium salt structure; 3) a unit containing an unsaturated bond structure; the unit containing a photosensitive structure is connected to the unit containing a quaternary ammonium salt structure at least via-C (=O)—, and the unit containing an unsaturated bond structure is connected to the unit containing a photosensitive structure at least via the unit containing a quaternary ammonium salt structure.

In the molecular structure of the water-soluble polymerizable is photosensitive monomer, apart from the photoinitiating unit (i.e. the unit containing a photosensitive structure), there is also quaternary ammonium salt ions and double bonds, so that the photosensitive monomer possesses both water solubility and polymerizability, not only owns good compatibility with the water-based resin, but also can polymerizes itself on the macromolecular chain of the resin, which effectively overcomes the defect that small molecules are easy to migrate to the surface of the product.

In one embodiment of the present disclosure, the unit containing the photosensitive structure is derived from a cleavable hydroxyphenone photoinitiator, preferably from substituted or unsubstituted α-hydroxyalkylbenzophenone photoinitiator. More specifically, the α-hydroxyalkylbenzophenone photoinitiator has the following structure:

wherein $R^1$, $R^2$ are independently selected from hydrogen, C1-C6 alkyls, phenyl, C1-C6 alkoxies or $R^1$, $R^2$ form a cyclohexyl ring together with the carbon atom to which they are attached; $R^3$ is selected from hydrogen, C1-C6 alkyls, C1-C6 alkoxies, C1-C6 hydroxyalkyls, —OCH$_2$CH$_2$— OR$_4$; $R_4$ is selected from hydrogen, C1-C6 alkyls.

Specifically, the α-hydroxyalkylphenone photoinitiator may be selected from the group consisting of 2-hydroxyl-2-methyl-1-phenyl-1-propanone, 1-hydroxyl-cyclohexyl-phenyl-ketone, 2-hydroxyl-4'-(2-hydroxyethoxy)-2-methyl-propiophenone, 2-hydroxyl-2-methyl-1-(4-isopropylphenyl)-1-propanone, 2-hydroxyl-2-methyl-1-(4-tert-butylphenyl)-1-propanone; preferably, selected from any one of 2-hydroxyl-2-methyl-1-phenyl-1-propanone, 1-hydroxycyclohexyl-phenyl-ketone, 2-hydroxyl-4'-(2-hydroxyethoxy)-2-methylpropiophenone, 2-hydroxyl-2-methyl-1-(4-isopropylphenyl)-1-propanone, 2-hydroxyl-2-methyl-1-(4-tert-butylphenyl)-1-propanone; from the point of view of improving initiation activity and yellowing resistance, 2-hydroxyl-4'-(2-hydroxyethoxy)-2-methylpropiophenone is is more preferable.

The α-hydroxyalkylphenone photoinitiator contains a carbonyl and an α-hydroxyl double active functional group, so that this type of photoinitiators has active chemical properties and has strong derivatization ability. This type of photoinitiators is not only suitable for general photopolymerization systems, but also is more applicable to emulsion or latex photopolymerization systems and water-soluble photopolymerization systems. This type of photoinitiators belongs to a cleavage-type free radical photoinitiator, but compared with other common cleavage-type photoinitiators such as benzoin ether, it has good yellowing resistance and thermal stability, and compared with hydrogen abstraction-type free radical photoinitiators such as benzophenone (BP), it has high photoinitiation activity and good yellowing resistance. The inventor of the present disclosure finds that when the photosensitive structure unit of the present disclosure is derived from the α-hydroxyalkylphenone photoinitiator, better photoinitiation efficiency, yellowing resistance and thermal stability can be obtained compared with other types of photoinitiators, moreover, the volatility can also be reduced, wherein the effect of 2-hydroxyl-4'-(2-hydroxyethoxy)-2-methylpropiophenone is particularly effective. The inventor speculates that because the benzene ring in its structure is directly connected to an oxygen atom, the two unique pairs of electrons on the oxygen atom can be conjugated with the benzene ring, so that the electron density of the benzene ring is increased, as a result, the probability of electrons being excited to transition is increased, and the benzene ring acts with other groups (such as nitrogen-containing groups, and unsaturated double bonds) to greatly improve the photoinitiation activity; and the reduction of volatility is related to the long side chain of the benzene ring. The presence of quaternary ammonium salt can greatly improve water solubility, while also having certain antibacterial property. The unit containing quaternary ammonium salt structure comprises a quaternary ammonium salt group, and may also comprises several alkylene groups.

The unit containing the unsaturated bond can be a polymerizable group containing double bonds. Such a reactive group can enable the is photosensitive unit to be incorporated into the main chain of the polymer by means of free radical polymerization in the form of a repetitive unit. The unit containing the unsaturated bond can be selected from units having (meth) acrylate groups. The presence of the polymerizable group can overcome the problems of toxicity and high migration rate of conventional small molecule photoinitiators, and promote the anchoring of the photoinitiators in a polymer network, can also improve the material properties through copolymerization with other monomers, and meanwhile inhibit undesirable volatilization caused by residual small molecule photoinitiators. In a preferred embodiment of the present disclosure, the unit containing the photosensitive structure is directly connected to the quaternary ammonium salt structure via carbonyl group (—C(=O)—), and the unit containing the unsaturated bond is directly connected to the unit containing the photosensitive structure via the structural unit containing the quaternary ammonium salt. This mode of connection provides the greatest opportunity for the interaction between various structural units, and is favorable for energy transfer, generates more and faster free radical species, thus improving the initiation efficiency.

In a preferred embodiment of the present disclosure, the water-soluble polymerizable photosensitive monomer has the following structural formula:

Formula (III)

wherein: $R_1$=$CH_3$ or H; $R_2$ and $R_3$ are each independently selected from a linear alkyl group having 1 to 20 C atoms or a branched alkyl group having 3 to 20 C atoms; X is halogen; n=1-10; m=1-4; f=1-3; Preferably, $R_2$ and $R_3$ are the same, X is bromine, n=1, m=1, f=1; More preferably, $R_2$ and $R_3$ are methyl or ethyl, X is bromine, n=1, m=1, f=1. The selection of groups and molecular chain lengths in the general formula is mainly based on the requirements of viscosity, initiation rate and mobility of the comprehensive product.

More preferably, a suitable water-soluble polymerizable photosensitive monomer according to the present disclosure comprises one or more compounds of the following structures:

The water-soluble polymerizable photosensitive monomer of the present disclosure is obtained by an acyl halogenation treatment on the molecular end of a compound containing photosensitive structure, followed by the reaction with a tertiary amine group-containing (meth) acrylate.

The reaction flow of an exemplary water-soluble polymerizable photosensitive monomer is as follows:

wherein $R_1$ and $R_2$ are the same as defined by formula (III).

The present disclosure finds that the molar fraction of the water-soluble polymerizable photosensitive monomer in the polymer, that is, a copolymer, will affect the lubricity of the hydrophilic coating prepared therefrom. If the molar fraction is too high, the content of the hydrophilic monomer is relatively reduced, the initial lubricity of the obtained hydrophilic coating is poor, and the friction force is high; and if the molar fraction is too low, the curing efficiency is affected, and as the number of cycles increases, the friction force of the coating will increase rapidly. In the present disclosure, the molar fraction of the water-soluble polymerizable photosensitive monomer in the copolymer is 0.08-12%, preferably 0.1-10%, further preferably 0.5-8%, more preferably 3-7.5%, and most preferably 3-5%. In a preferred embodiment of the present disclosure, the molar fraction of the water-soluble polymerizable photosensitive monomer in the copolymer is 4%. By using the specific is mole fraction, the lowest friction force can be obtained, and the friction force hardly increases with the number of cycles. However, the friction force is not increased after more than 30 cycles.

Hydrophilic Monomer

The hydrophilic monomer refers to a monomer that can dissolve more than 1 g in 100 g water at 25° C. The hydrophilic photocurable polymer can be obtained by copolymerization of water-soluble polymerizable photosensitive monomer and hydrophilic monomer. The hydrophilic monomer is mainly used to provide hydrophilicity to the polymer.

The hydrophilic monomer includes one or more of the following compounds: unsaturated carboxylic acid or carboxylate, unsaturated carboxylic acid ester, unsaturated acid hydroxyalkyl ester, unsaturated anhydride, unsaturated amide, unsaturated lactam, and epoxyalkane.

By way of example, the hydrophilic monomer includes, but is not limited to, one or more of the following compounds: (meth) acrylic acid, (meth) acrylamide, vinylpyrrolidone, (meth) acrylate hydroxyethyl (propyl) ester, vinyl acetate, ethylene oxide, maleic acid, maleic anhydride, fumaric acid, fumaric anhydride, dimethacrylamide; preferably, the hydrophilic monomer includes one or more of the following compounds: acrylic acid, acrylamide, dimethacrylamide, hydroxyethyl acrylate, and vinylpyrrolidone.

Among the hydrophilic monomers mentioned above, vinyl pyrrolidone (NVP) and polymer thereof possess special properties thanks to their structures. NVP is easy to polymerize, and the polymer derived from it has excellent hydrophilicity, complexing ability, physiological compatibility, and chemical stability, with low toxicity and no irritation to skin; The vinyl pyrrolidone has strong solubilization effect, can increase the water solubility of some pharmacologically active substances that are basically insoluble in water, and is suitable for medical use. As such, a more preferable hydrophilic monomer of the present disclosure is vinyl pyrrolidone. It is also surprisingly found that when vinyl pyrrolidone is is used as the hydrophilic monomer, the resultant hydrophilic coating has a better lubrication effect, which is highlighted by low friction force and no change in friction force with the increase of cycle number.

Polymerization

The photocurable polymer according to that present disclosure is prepared by free radical polymerization procedure, including but not limited to conventional free radical polymerization, active controllable free radical polymerization, preferably, the curable hydrophilic polymer is prepared by a conventional free radical polymerization method. The photocurable polymer is prepared in a certain medium, including but not limited to solution polymerization, emulsion polymerization, inverse emulsion polymerization, suspension polymerization, bulk polymerization. Preferably, from the point of view of easy operation, the photocurable hydrophilic polymer is completed by solution polymerization, more preferably, from the point of view of environmental protection, the photocurable polymer is accomplished by co-polymerization in aqueous solution. In one embodiment of the present disclosure, the water-soluble polymerizable photosensitive monomer and the hydrophilic monomer are dissolved in water, and a free radical initiator is added to the system, and oxygen is removed, and a reaction is carried out at a specific temperature to obtain a photocurable polymer.

The concentration of the monomer contained in the aqueous solution is preferably between 10% and 50%, more preferably between 10% and 30%, and even more preferably between 12% and 20%, relative to the weight of solution.

The free radical initiator in polymerization reaction refers to a substance that can generate free radicals when activation energy is applied, and includes a thermal activation initiator, such as organic peroxides, organic hydrogen peroxide and azoic compounds. Representative examples of such initiators include, but are not limited to, benzoyl peroxide, tert-butyl, perbenzoate, diisopropyl, peroxydicarbonate, cumene is hydroperoxide, azobisisobutyronitrile, etc. In a preferred embodiment of the present disclosure, the free radical initiator is azobisisobutyronitrile. The thermal initiator is usually used in an amount of 0.01 to 5% relative to the mass of monomer, preferably 0.02 to 0.05%.

In order to reduce the mobility, the photocurable polymer preferably has a number-average molecular weight of at least 2,000, a photocurable polymer having a relatively high molecular weight is preferred, but for the ease of application of the coating, the molecular weight is preferably 1.5 million or less. The present disclosure also finds that the molecular weight of the photocurable polymer will affect the lubricity of the hydrophilic coating. In order to obtain a hydrophilic coating that has good lubricity after multiple cycles, the number-average molecular weight of the photocurable polymer is preferably 0.005-1 million, further preferably 0.02-0.8 million, more preferably 0.05-0.6 million, and most preferably 0.1-0.5 million.

Coating Composition

The coating composition of the present disclosure comprises at least one photosensitive functional compound and at least one photocurable polymer above-mentioned.

The content of the photosensitive functional compound is from 10 to 50%, preferably from 15 to 40%, and further preferably from 15 to 25% by mass, based on the total dry mass of the coating composition. Furthermore, in some embodiments of the disclosure, the solid content of the coating composition is from 0.1 to 20%, preferably 1 to 10%, more preferably 2 to 8%, and further preferably 2.5 to 7.5%.

In addition, the coating composition of the present disclosure may include a solvent and optionally other hydrophilic polymers. For solvents, in some embodiments of the present disclosure, it may be from 60 to 99.9%, preferably from 75 to 98%, more preferably from 90 to 95%, relative to the total mass of coating composition.

The hydrophilic polymer refers to a linear, branched or cross-linked is polymer having a high molecular weight and composed of macromolecules, and the polymer has affinity for water or other polar liquid and can provide hydrophilicity for the coating. The hydrophilic polymer can be synthetic or derived from natural products. The hydrophilic polymer can be a homopolymer, a copolymer or a blend. The hydrophilic polymer includes, but not limited to, one or more of homopolymers of polylactam (such as polyvinylpyrrolidone), polyurethane and (meth) acrylic acid (sodium) or copolymers with other monomers, copolymers of polyvinyl alcohol and polyvinyl ether or with other monomers, maleic acid (anhydride) copolymer, homopolymers of polyester, polyacrylate and acrylamide or copolymers with other monomers, homopolymers of polyoxyethylene, polyamide and sulfonic acid (salt) or copolymers with other monomers, cellulose and its derivatives, polysaccharides (chitin, chitosan, hyaluronic acid (sodium), alginic acid (sodium)), and polypeptides. In order to ensure the hydrophilic lubricity of the coating, preferably, the hydrophilic polymer includes one or more of polyacrylamide, polyvinyl pyrrolidone, polyoxyethylene, hyaluronic acid and polyacrylic acid, and more preferably, the hydrophilic polymer includes one or more of polyoxyethylene, polyacrylamide and polyvinyl pyrrolidone.

To ensure the hydrophilicity and firmness of the coating, the molecular weight of the hydrophilic polymer is at least 1000, preferably at least 5000, preferably at least 10,000, preferably at least 100,000. In order to ensure the process operability of the masking liquid, the molecular weight of hydrophilic polymer is at most 5 million, preferably at most 3 million, preferably at most 2 million, preferably at most 1.5 million.

The hydrophilic polymer in the coating composition is in a mass fraction ranging from 0 to 20%, preferably from 0.1 to 10%, further preferably from 0.1 to 5%, more preferably from 0.1 to 2.5%, most preferably from 0.1 to 1%, further, in a mass fraction ranging from 0.1 to 0.5%.

Any solvent that allows coating of a coating composition with is hydrophilicity on the surface is suitable for use in the present disclosure. Preferably, the solvent is one solvent or a mixed solvent in which the above-mentioned photosensitive functional compound, photocurable polymer and hydrophilic polymer can be dissolved to form a homogeneous solution. The example of the solvent includes one or more of water, low molecular weight alcohols (methanol, ethanol, isopropanol, butanol, pentanol, ethylene glycol, propylene glycol, glycerol or the like), ethyl acetate, n-hexane, methylene, chloride, chloroform, N,N-dimethylformamide, N,N-dimethylacetamide, dimethyl sulfoxide, acetone, ether, toluene, benzene, xylene, cyclohexane, phenol. The low-cost and pollution-free solvent suitable for dissolving and mixing uniform formulations is preferably a mixture of water and isopropanol, preferably, the volume ratio of water to isopropanol is 1:10 to 10:1, suitable for dissolving and mixing uniform formulations, the volume ratio of water to isopropanol is more preferably 1:5 to 5:1, and is most preferably 2:3 to 3:2.

In addition, lubricating additives such as surfactant, wax, lubricant, soap and detergent can be added to the coating composition as needed. These lubricating additives will not increase the osmolarity of the coating too much, but can increase the lubricity when wetting and reduce the adhesion. Their low solubility in water helps to keep them in the coating. Other additives can include supporting polymers, polyelectrolytes, wetting agents, leveling agents, defoamers, film forming aids, thickeners, pigments, antibacterial agents, colorants, surfactants, and the like. In a specific embodiment of the present disclosure, the coating composition can obtain good lubricity and firmness without adding additional optional ingredients except for the photocurable polymer, the solvent and the optional hydrophilic polymer.

Formation of Surface Coating of Central Venous Catheter

In the present disclosure, the coating composition according to the present disclosure is coated on the surface of the central venous catheter by one or more methods of brushing, dipping, spraying, pouring, scraping, followed by curing on the surface of the central venous catheter, and a central venous catheter with a very lubricious tactility can be provided, it can be easily inserted into body tissues or cavities, and maintains hydrophilicity and lubricity even after contacting with tissues for a long period of time, it can also be easily taken out, while no coating falls off, the degree of lubricity does not decrease, and the firmness remains excellent after repeated friction for 30 times in a simulated human tissue environment. According to a specific embodiment of the disclosure, the coating possesses excellent firmness, if there is no obvious increase in friction force after 30 cycles. It is known in the art that if the friction force of the coating increases, it suggests that the coating falls off and the firmness gets worse; If the friction force does not increase significantly, it suggests that the coating does not fall off and remains firm.

Preferably, the coating composition of the present disclosure is coated by scraping, dipping methods; most preferably, the coating composition of the present disclosure is applied to the surface of the central venous catheter by dipping to obtain a coating with relatively uniform thickness. The light source used in the curing procedure of the present disclosure includes any one of the following sources: UV light source, visible light source and infrared light source; preferably, the light source is UV light source and visible light source; more preferably, UV light source. Preferably, the intensity of ultraviolet light source at the time of curing is 5 to 25 mW/cm$^2$, and the time for curing of coating composition is 2 to 7 minutes, preferably 3 to 5 minutes. The thickness of the hydrophilic coating can be controlled by changing immersion time, traction rate or the viscosity of coating composition and the number of coating steps. In the present disclosure, the thickness of the hydrophilic lubricious coating of the central venous catheter is in the range of 2 to 15 μm, most preferably in the range of 2 to 10 μm. When the thickness of the coating is less than 2 μm, the coating cannot achieve good water absorption and retention, resulting is in a poor swelling effect, and good water absorption and lubrication effect and expected anti-thrombotic/thrombolytic ability cannot be attained; However, when the thickness of the coating is higher than 15 μm, the curing of the coating is incomplete, which easily leads to a poor gelation of the coating, resulting in the reduction of overall firmness of the coating. The cured polymer is easy to dissociate during use, resulting in residence and pollution, which reduces the durability of lubricity and safety of the coating.

In one embodiment of the present disclosure, the central venous catheter is immersed in a cartridge containing the coating composition of the present disclosure, left for 0.1 to 2 min, then the catheter was lifted at a speed of 0.5 to 1 cm/s, and the catheter with masking liquid was irradiated with an ultraviolet lamp for 3 to 5 min for curing treatment, then the cured sample was placed in air to dry to obtain the central venous catheter with hydrophilic lubricious coating.

The Second Embodiment

In the second embodiment of the present disclosure, there provided a medical device comprising the above-said central venous catheter with coating formed on its surface.

"Medical device" in the present disclosure should be construed in a broad sense. The medical device can be an implantable device or an external device, which can be used temporarily or implanted permanently into the human body.

Example

Examples are described below to illustrate the present disclosure. Those skilled in the art will appreciate that the example is merely illustrative and not exhaustive.

Synthesis of Lysyl Benzophenone (1) Synthesis of 4-Benzoyl Chlorobenzoic Acid.

Solution A: oxalyl chloride in dichloromethane (0.12 g/mL), solution B: 4-benzoylbenzoic acid (0.067 g/mL) and anhydrous N, N'-dimethylformamide (0.33 μL/mL) in dichloromethane were prepared. In an ice bath, solution A was slowly added to solution B. The reaction was carried out overnight at room temperature, and the solvent was removed by rotary evaporation to obtain the product 4-benzoylchlorobenzoic acid.

(2) Synthesis of Boc-Lysyl Benzophenone.

2 g of Boc-lysine was weighed and dissolved in a mixed solution of 20 mL of dichloromethane and 2 mL of triethylamine, then 2 mL of 4-benzoyl chloride benzoic acid in dichloromethane solution was added dropwise under the condition of ice bath. After addition, the reaction was carried out overnight at room temperature to obtain the product Boc-lysine benzophenone.

(3) Synthesis of Lysyl Benzophenone.

1.0 g Boc-lysyl benzophenone was weighed and dissolved in 8 mL 1, 4-dioxane, then 5 mL HCl was slowly added dropwise, and reaction was carried out at 25° C. for 6 hours. The solvent was removed by rotary evaporation and dried in vacuum for 24 hours to obtain white solid lysyl benzophenone.

Preparation of Water-Soluble Polymerizable Photosensitive Monomer

Weighing 22.4 g (100 mmol) of 2-hydroxyl-4'-(2-hydroxyethoxy)-2-methylpropiophenone, 10.6 g (105 mmol) of triethylamine and 100 mL dichloromethane, placing the ingredients in a 250 mL flask, and placing the flask in an ice-water bath to fully dissolve the ingredients. Slowly dripping 9.1 mL of dichloromethane solution of bromoacetyl bromide (21.1 g, 105 mmol) into the flask within 1 h. After reacting for 0.5 h under an ice bath condition, heating up to room temperature to continue the reaction for 10 h. After the reaction is completed, cooling to room temperature and is dissolving the crude product in dichloromethane, washing with saturated saline solution, hydrochloric acid (1 M) and saturated sodium bicarbonate successively twice, drying over overnight via anhydrous magnesium sulfate, filtering and spin drying the solvent, using ethyl acetate and n-hexane as eluents, and obtaining 28.8 g of 2-hydroxyl-4'-(2-hydroxyethoxy bromoacetate)-2-methylpropiophenone after purification by column chromatography, wherein the product is a white solid, and the yield is 84%.

Dissolving 6.9 g (20 mmol) of 2-hydroxyl-4'-(2-hydroxyethoxy bromoacetate)-2-methylpropiophenone and 0.05 g of hydroquinone in 50 mL of acetonitrile, placing the solution in a 250 mL flask to fully dissolve the ingredients. Slowly dripping 50 mL of acetonitrile solution of dimethylaminoethyl methacrylate (3.2 g, 20 mmol) into the flask, and heating up to 60° C. to react for 12 h. After the reaction is completed, spin drying the solvent, precipitating the product with anhydrous ether, and obtaining 10 g of water-soluble polymerizable photosensitive monomer after purification by column chromatography.

Synthesis of Photocurable Polymer

Weighing 106.7 g (0.96 mol) of vinyl pyrrolidone, 16.9 g (0.04 mol) of water-soluble polymerizable photosensitive monomer and 0.0618 g (0.05% by mass fraction of total monomer) azodiisobutyronitrile and adding the same into a 1 L round-bottom flask, adding 700 mL of deionized water, and performing mechanical stirring to dissolve the ingredients. Filling $N_2$ to deoxidize the solution for 30 min, and placing the reaction flask in an oil bath to heat at 65° C. so as to start the reaction. After 6 hours of reaction, taking off and cooling the reaction solution to room temperature, precipitating the solution with 95% ethanol, and drying the precipitate in an oven at 35° C. in the dark for 36 h.

Preparation of Hydrophilic Lubricious Coating with Anticoagulant and Thrombolytic Effects Weighing 3 g of lysyl benzophenone and 5 g of photocurable polymer and dissolving the same in 95 g of deionized water/isopropanol mixed solvent, and stirring for 18 h in the dark to obtain colorless and clear masking liquid. Wiping the surface of the central venous catheter clean with a dust-free paper dipped in 75% ethanol, and drying the central venous catheter. Dipping the catheter into a charging cartridge containing the above-mentioned masking liquid, left for 1 min, lifting the catheter at a speed of 0.5 cm/s, and irradiating the catheter with the masking liquid with a UV lamp for 5 min for curing treatment, wherein the UV intensity is 10 mW/cm$^2$, the rotation speed of the catheter is 4 rpm. The cured sample is placed in the air for drying.

<Lubricity Test>

The coated or uncoated central venous catheter was placed in a clip friction tester to test the lubrication performance. Specifically, the catheter was clamped by double clips, the clips were placed in deionized water, and the force required to pull the catheter was tested to obtain the results of lubrication performance. The clamping force used was 300 g, the lifting speed was 10 cm/s, and the test cycle was 30 times. The test results are shown in Table 1, wherein the items "polyurethane (PU)" and "silica gel" are the results without the coating of the present disclosure:

TABLE 1

Lubrication performance of central venous catheter of different materials

| Material of central venous catheter | Initial friction force (N) | Friction force of 30$^{th}$ cycle (N) | Friction force of 30$^{th}$ cycle/Initial friction force |
|---|---|---|---|
| Polyurethane (PU) | 0.254 | 3.450 | 13.58 |
| Silica gel | 0.225 | 3.280 | 14.58 |
| Polyurethane + coating | 0.124 | 0.140 | 1.13 |
| Silica gel + coating | 0.128 | 0.250 | 1.95 |

<Fibrinogen Adsorption Test>

Fibrinogen was labeled with $^{125}$I by iodine chloride (ICl) method, and was passed through AG1-X4 anion exchange resin column to remove free iodine. The labeled protein was added to platelet-free plasma at a concentration of about 10% relative to that of fibrinogen in normal plasma. A central venous catheter with a length of 1 cm was put into the above protein solution for 3 h, and was rinsed with phosphate buffer solution three times, each for 10 minute. After being blotted dry with filter paper, it was transferred to a clean tube and tested by automatic gamma counter. The amount of protein adsorption was expressed in terms of mass per unit area.

Figure 1:
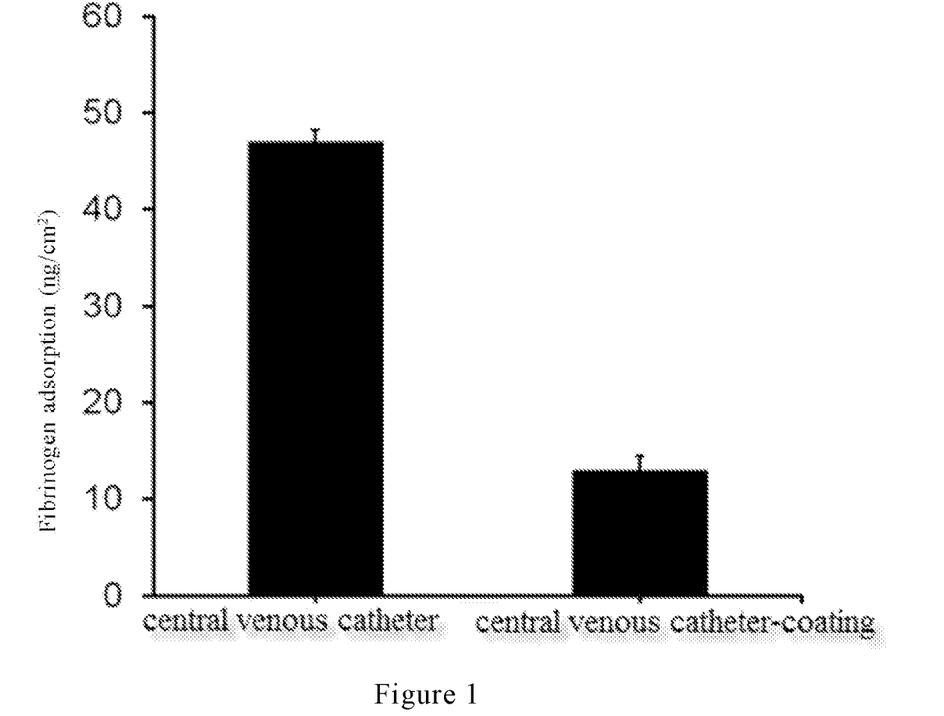
FIG. 1: Amount of fibrinogen adsorption on the surface of central venous catheter before and after application of hydrophilic lubricious coating.

See FIG. 1 for the test results. Figure. 1 shows the amount of fibrinogen adsorbed on the surface of the central venous catheter before and after application of the hydrophilic lubricious coating. The thrombusis on the surface of implanted materials starts from the accumulation of fibrin and other proteins on the surface of materials. The accumulation of anti-nonspecific proteins on the surface of materials can effectively reduce the probability and time of thrombus formation. Fibrinogen is used here as a model protein to detect the ability of the catheter surface to resist non-specific protein adsorption after being coated with hydrophilic lubricious coating.

<Plasminogen Adsorption Test>

Plasminogen was labelled with $^{125}$I by iodogen method, and was dialyzed overnight against three changes of PBS (pH 7.4) to remove free iodine. The labeled protein was added to platelet-free plasma at a concentration of about 10% relative to that of plasminogen in normal plasma. A central venous catheter with a length of 1 cm was put into the above protein solution for 3 hours, and was rinsed with phosphate buffer solution three times, each for 10 min. After being blotted dry with filter paper, it was transferred to a clean tube and tested by automatic gamma counter. The amount of protein adsorption was expressed in terms of mass per unit area.

Figure 2:
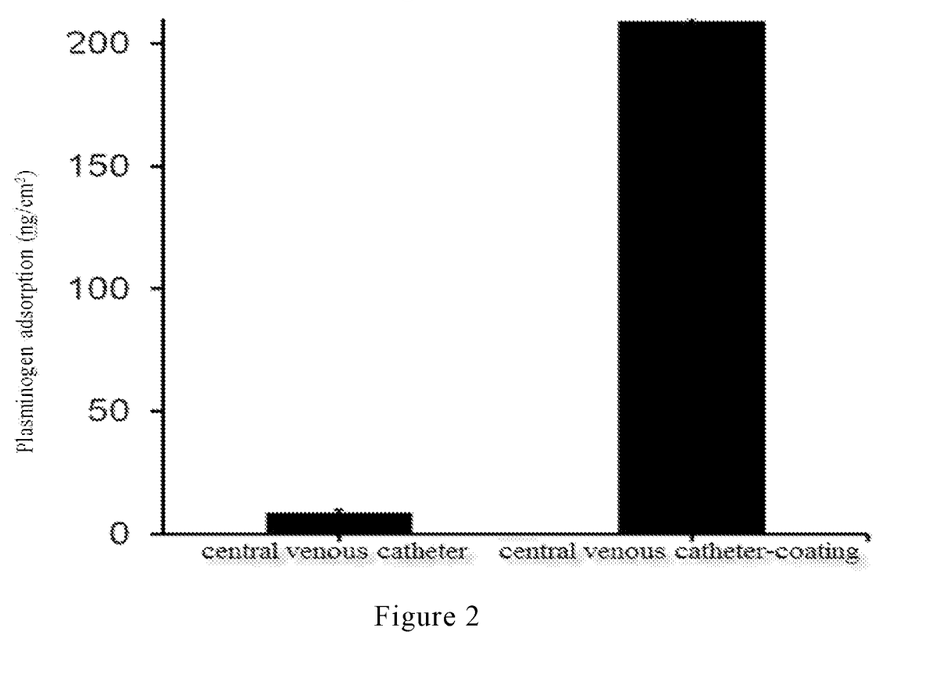
FIG. 2: Amount of plasminogen adsorption on the surface of central venous catheter before and after application of the hydrophilic lubricate coating.

See FIG. 2 for the test results. FIG. 2 shows the amount of plasminogen adsorbed on the surface of the central venous catheter before and after application of the hydrophilic lubricate coating. Lysine in the coating can promote the adsorption of t-PA of plasminogen, thus generating plasminolytic enzyme and dissolving primary thrombus. As can be seen from the chart, the capacity for plasminogen adsorption of the surface of the central venous catheter after applying the hydrophilic coating is greatly increased.

<Thrombolysis Test>

A sample of central venous catheter with a length of about 0.5 cm was soaked in trimethylol aminomethane buffer (pH=7.4) for 1 h. At the end of 1 h, it was taken out and soaked in common human plasma for 3 h. Afterwards, it was rinsed with trimethylol aminomethane buffer three times, and was soaked in t-PA for 10 min, rinsed again with trimethylol aminomethane buffer 3 times, and was blotted dry with filter paper, then was added in sequence 100 μL plasma, and 100 μL 0.025 M calcium chloride solution. All the soakings above were carried out in a 37° C. constant temperature incubator, and the added plasma and t-PA need to be preheated in a 37° C. incubator in advance. The absorption at 405 nm was measured by microplate reader, the time interval was set at 30 s, and the total test time should not be less than 1 h.

Figure 3:
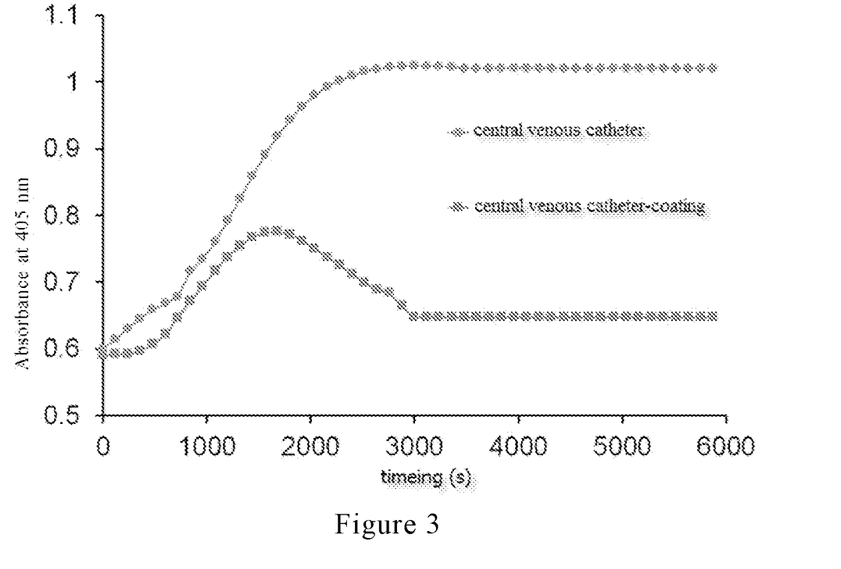
FIG. 3: Thrombolytic ability of the surface of central venous catheter before and after application of the hydrophilic lubricious coating.

See FIG. 3 for the test results. FIG. 3 shows the thrombolytic capability of the surface of central venous catheter before and after application of hydrophilic lubricate coating. With the extension of time, the absorbance gradually increased until the maximum, indicating that thrombus was completely formed during this period. After the thrombus was completely formed, the absorbance of the coated central venous is catheter gradually decreased, demonstrating that the thrombus was being dissolved. After the thrombus completely dissolved, the absorbance returned to the initial value. It demonstrates that the coating endows the surface of the catheter with certain thrombolytic ability.

INDUSTRIAL AVAILABILITY

The present disclosure provides an industrially manufacturable central venous catheter for medical use.

The invention claimed is:

1. A central venous catheter, comprising: a tube body and a coating formed on the surface of the tube body, the coating being formed of a coating composition comprising at least one photosensitive functional compound and at least one photocurable polymer, wherein the photosensitive functional compound has a structure of formula (I):

P-L-I (I)

wherein

P represents a photosensitive structural part, L represents a divalent linking group, and I represents a lysine residue, the photocurable polymer is copolymerized by ingredients comprising water-soluble polymerizable photosensitive monomer and a hydrophilic monomer, the water-soluble polymerizable photosensitive monomer comprises: 1) a unit containing a photosensitive structure; 2) a unit containing a quaternary ammonium salt structure; and 3) a unit containing an unsaturated bond structure;

the unit containing a photosensitive structure is connected to the unit containing the quaternary ammonium salt structure at least via —C(=O)—, and the unit containing the unsaturated bond structure is connected to the unit containing a photosensitive structure via the unit containing the quaternary ammonium salt structure.

2. The central venous catheter according to claim 1, wherein in the photosensitive functional compound:

P is derived from an aromatic ketone photosensitive structure;

the divalent linking group L is selected from groups consisting of —CO— and —O—;

I is connected to L by a nitrogen atom in lysine.

3. The central venous catheter according to claim 1, wherein the photosensitive functional compound has a structure represented by formula (II):

(II)

4. The central venous catheter according to claim 1, wherein 1) unit containing a photosensitive structure in the water-soluble polymerizable photosensitive monomer is derived from substituted or unsubstituted a-hydroxyalkyl-benzophenone photoinitiator; and 3) unit containing an unsaturated bond structure is selected from units containing (meth) acrylate groups.

5. The central venous catheter according to claim 1, wherein the water-soluble photosensitive monomer has a structure of formula (III):

(III)

wherein: $R_1=CH_3$ or H; $R_2$ and $R_3$ are each independently selected from a linear alkyl group having 1 to 20 C atoms or a branched alkyl group having 3 to 20 C atoms; X is halogen; n=1-10; m=1-4; f=1 3.

6. The central venous catheter according to claim 1, wherein the hydrophilic monomer comprises one or more of the following compounds: unsaturated carboxylic acid or carboxylate, unsaturated carboxylic acid ester, unsaturated acid hydroxyalkyl ester, unsaturated anhydride, unsaturated amide, unsaturated lactam and epoxyalkane.

7. The central venous catheter according to claim 1, wherein the molar fraction of the water-soluble polymerizable photosensitive monomer in the photocurable polymer is 0.08-12%; the number-average molecular weight of the photocurable polymer ranges from 0.002 to 1.5 million.

8. The central venous catheter according to claim 1, wherein the content of the photosensitive functional compound in the coating composition is from 10 to 50%, relative to the total dry weight.

9. A method for producing a central venous catheter according to claim 1, comprising: forming the coating composition on the surface of the central venous catheter body and performing curing under light condition.

10. A medical device, comprising the central venous catheter according to claim 1.

11. The central venous catheter according to claim 2, wherein in the photosensitive functional compound:
P is derived from one of the following compounds: substituted or unsubstituted benzophenone, substituted or unsubstituted acetophenone, substituted or unsubstituted thioxanthone, substituted or unsubstituted xanthone, substituted or unsubstituted fluorenone and derivatives thereof.

12. The central venous catheter according to claim 4, wherein 1) unit containing a photosensitive structure in the water-soluble polymerizable photosensitive monomer is derived from any one of 2-hydroxyl-2-methyl-1-phenyl-1-propanone, 1-hydroxyl-cyclohexyl-phenyl-ketone, 2-hydroxyl-4'-(2-hydroxyethoxy)-2-methylpropiophenone, 2-hydroxyl-2-methyl-1-(4-isopropylphenyl)-1-propanone, 2-hydroxyl-2-methyl-1-(4-tert-butylphenyl)-1-propanone.

13. The central venous catheter according to claim 4, wherein 1) unit containing a photosensitive structure in the water-soluble polymerizable photosensitive monomer is derived from 2-hydroxy-4'-(2-hydroxyethoxy)-2-methyl-propiophenone.

14. The central venous catheter according to claim 5, wherein $R_2$ and $R_3$ are identical, X is bromine, n=1, m=1, f=1.

15. The central venous catheter according to claim 5, wherein $R_2$ and $R_3$ are both methyl or ethyl, X is bromine, n=1, m=1, f=1.

16. The central venous catheter according to claim 6, wherein the hydrophilic monomer includes one or more of the following compounds: (meth)acrylic acid, (meth)acrylamide, vinyl pyrrolidone, (meth) acrylate hydroxyethyl ester, (meth) acrylate hydrolpropyl ester and dimethacrylamide.

17. The central venous catheter according to claim 6, wherein the hydrophilic monomer is selected from vinyl pyrrolidone.

* * * * *